(12) United States Patent
Hartwig et al.

(10) Patent No.: US 12,196,450 B2
(45) Date of Patent: Jan. 14, 2025

(54) OPTICAL ARRANGEMENT FOR DISINFECTION IN APPARATUSES OPERATING WITH AIR OR A LIQUID

(71) Applicant: OSRAM GmbH, Munich (DE)

(72) Inventors: Ulrich Hartwig, Berlin (DE); Norbert Magg, Berlin (DE)

(73) Assignee: OSRAM GMBH, Munich (DE)

( * ) Notice: Subject to any disclaimer, the term of this patent is extended or adjusted under 35 U.S.C. 154(b) by 327 days.

(21) Appl. No.: 17/722,091

(22) Filed: Apr. 15, 2022

(65) Prior Publication Data
US 2022/0341608 A1    Oct. 27, 2022

(30) Foreign Application Priority Data

Apr. 23, 2021 (DE) ............... 10 2021 204 070.5

(51) Int. Cl.
| | |
|---|---|
| F24F 8/22 | (2021.01) |
| A61L 2/10 | (2006.01) |
| F21V 7/10 | (2006.01) |
| G02B 6/32 | (2006.01) |
| G02B 19/00 | (2006.01) |

(Continued)

(52) U.S. Cl.
CPC ............... *F24F 8/22* (2021.01); *A61L 2/10* (2013.01); *F21V 7/10* (2013.01); *G02B 6/32* (2013.01); *G02B 19/0019* (2013.01); *G02B 27/30* (2013.01); *F21Y 2115/10* (2016.08)

(58) Field of Classification Search
CPC ...... F24F 8/22; A61L 2/10; F21V 7/10; G02B 6/32; G02B 19/0019; G02B 27/30
See application file for complete search history.

(56) References Cited

U.S. PATENT DOCUMENTS

| | | | |
|---|---|---|---|
| 6,468,433 B1* | 10/2002 | Tribelski | A61L 2/10 |
| | | | 205/435 |
| 2006/0104859 A1* | 5/2006 | Tribelsky | A23L 3/28 |
| | | | 250/455.11 |

(Continued)

FOREIGN PATENT DOCUMENTS

| | | |
|---|---|---|
| DE | 102017112460 A1 | 1/2018 |
| DE | 102017220338 A1 | 5/2019 |
| DE | 102018222307 A1 | 6/2020 |

(Continued)

OTHER PUBLICATIONS

Norm DIN 5031-7 1984-01-00. Optical Radiation Physics and Illumination Engineering; Terms for Wavebands.

*Primary Examiner* — Evan P Dzierzynski
*Assistant Examiner* — Nathaniel J Lee
(74) *Attorney, Agent, or Firm* — ArentFox Schiff LLP

(57) ABSTRACT

An optical arrangement for disinfection in apparatuses operating with air or a liquid comprises at least one radiation source or at least one group of radiation sources, which emits or jointly emit radiation in the ultraviolet wavelength range, at least one beam collecting optical unit, which collects the radiation emitted by the radiation source or the group of radiation sources, a number of beam delivering optical units, each configured to receive the radiation collected by the at least one beam collecting optical unit, and also a number of effect zones spatially separated from one another, into which the radiation delivered via the beam delivering optical units is emitted in order to bring about a disinfecting effect.

14 Claims, 9 Drawing Sheets

(51) Int. Cl.
*G02B 27/30* (2006.01)
*F21Y 115/10* (2016.01)

(56) References Cited

U.S. PATENT DOCUMENTS

2016/0088868 A1* 3/2016 Dobrinsky ............... A23L 3/28
　　　　　　　　　　　　　　　　　　　　　　　250/492.1
2018/0140726 A1　　5/2018 Shur et al.

FOREIGN PATENT DOCUMENTS

EP　　　2521940 B1　　4/2014
EP　　　1915086 B1　　10/2016

* cited by examiner

OPTICAL ARRANGEMENT FOR DISINFECTION IN APPARATUSES OPERATING WITH AIR OR A LIQUID

This application claims priority to German Patent Application 10 2021 204 070.5, filed on Apr. 23, 2021, the contents of which are hereby incorporated by reference in their entireties.

TECHNICAL FIELD

The present invention relates to an optical arrangement for disinfection in apparatuses operating with air or a liquid such as water, for instance, in particular dishwashers, washing machines, air-conditioning systems, ventilation systems, air circulation systems, air dehumidifiers or air humidifiers. Such optical arrangements have radiation sources configured to emit radiation having wavelengths in the range of UV radiation, in particular UV-C radiation, into an interior of the apparatus or into a container connected thereto in order to manifest their intended effect in the corresponding zones of the apparatus, in particular to irradiate and thereby disinfect surfaces, liquids or air contaminated with germs.

PRIOR ART

It is known to carry out disinfection or sterilization of gases such as air, liquids or surfaces of solid media with the aid of UV radiation sources, in particular also increasingly available LED-based UV radiation sources. The UV radiation acting on the relevant liquid makes it possible here to inactivate microorganisms contained therein, in particular viruses, bacteria or fungi. In this case, the corresponding germs are either directly killed by the UV radiation or at least damaged with regard to their DNA and thus prevented from replicating. What proves to be particularly effective here is the radiation in the wavelength range of 200 nm to 280 nm, which is also referred to as far UV radiation in accordance with DIN 5031-7, and also the adjacent range of 100 nm to 200 nm, which is accordingly referred to as vacuum UV radiation. Both wavelength ranges taken together are generally referred to as UV-C radiation. Furthermore, UV radiation in the range of 249 nm to 338 nm is effective vis-à-vis bacteria on biofilms, the wavelength range of between 292 nm and 306 nm being distinguished by a particularly high efficacy, with an efficacy maximum at 296 nm. The treatment of biofilms is concomitantly included here. Radiation of this wavelength is absorbed in the Earth's atmosphere, with the result that most microorganisms have not formed any resistance to it. DNA absorbs radiation in particular at a maximum lying at approximately 260 to 270 nm. The wavelength ranges mentioned are referred to in combination herein as UV-C radiation and are predominantly used in UV reactors. For the purposes of this application, the term UV-C radiation also covers the range of 10 nm to 121 nm (extreme ultraviolet).

Consequently, LEDs which emit radiation in the UV-C wavelength range, in particular, are used for the sterilization of fluids, surfaces of solid media etc. While the service lives can amount to tens of thousands of hours, the so-called wall plug efficiency (radiation emitted per unit of energy used) of the LEDs in the UV-C range is however currently still significantly less than that of low-pressure mercury lamps or other UV lamps (e.g. approximately 3%, but up to 6%, as opposed to 30% to 50%), the efficiency even still decreasing dramatically toward shorter and shorter wavelengths, even though progress continues to be achieved.

Further advantages of LED-based radiation sources concern, inter alia, the lower power consumption, less evolution of heat, a higher shock resistance and primarily also a smaller space requirement or structural space in comparison with UV gas discharge lamps, for example.

However, there are still the disadvantages of the achievable amounts of radiation still being rather low or the comparatively high costs per mW of radiation power. Accordingly, UV disinfection systems have to be designed efficiently for a successful application in practice. Therefore, hitherto endeavors have been made predominantly to the effect of attempting to attain a high system efficiency by optimizing factors such as the wall plug efficiency of the UV LED radiation sources, the efficiency of the reactor (e.g. design of the interior or operating modes), the coupling of the radiation into the reactor (e.g. arrangement and alignment of the LEDs and also reactor walls) and the distribution of the radiation in the reactor.

In many places, however, applications also consist in using UV radiation for the purpose of disinfection or sterilization in a plurality of regions that are spatially at a distance from one another. These may be for example domestic appliances such as, for instance, washing machines, dishwashers, or the like, in which liquids contaminated with germs are circulated in a circuit by pumping, for example a washing liquor consisting of water, dissolved dirt particles and germs dissolved in the water or adhering to the dirt particles. In this case, the objective of sterilization concerns not only the liquids in the different regions, but also such regions within the respective apparatus in which surfaces are themselves contaminated by at least temporary contact with the contaminated liquid.

Furthermore, it may be advantageous to treat not only the washing liquor or contaminated surfaces with UV radiation, but also the relevant washware itself, e.g. laundry in the wash drum or dishes in the interior of the dishwasher. Furthermore, in order to support the disinfection effect, in addition ozone can also be introduced into the washing liquor before, during or after a process of UV disinfection of the washing liquor, wherein UV radiation can indeed also be used in turn for producing the ozone.

The document EP 1 915 086 B1 can be cited as an example in this respect, said document showing e.g. in FIG. 1, 3 or 4 depicted therein a dishwasher with quite a few sensitive regions in which cavities or surfaces coming into contact with contaminated liquid would appear to be entirely suitable for UV disinfection. The document merely proposes mounting a UV lamp in the vicinity of a filter device which filters e.g. relatively coarse food remains etc. out of the washing liquid circulating between tub interior, pump sump, washing pump, feed line for the washing arms and tub interior again and is therefore suitable for sterilization as the most sensitive region. Nevertheless, there may however also be a desire for additional disinfection of the regions mentioned but rather also the dish racks or the extraction pump for draining the liquid from the apparatus, etc. In all these regions contamination can take place and direct irradiation in the UV wavelength range or the addition of ozone produced by UV radiation, etc. can thus be usable in an advantageous manner.

A further application example for the multiple use of UV radiation sources is ventilation and air-conditioning systems, e.g. air-conditioning systems or air-conditioners, ventilation systems or air circulation systems, etc. Here, too, there are generally a plurality of regions which are spatially separated and/or at a distance from one another and in which contaminations can occur and in which UV radiation can therefore be used for sterilization. Such sensitive regions are for example moist system parts such as those used for condensation, dehumidifiers or humidifiers, heat exchangers, filters (e.g. HEPA), regions with inadequate throughflow or subjected to a great contamination burden, such as edges, corners and the like.

In this case, however, the UV radiation sources can each only ever be configured for exactly one irradiation task in a spatially delimited effect zone, e.g. for sterilization near the filter device or for producing ozone in a separate reactor. Accordingly, an apparatus such as a dishwasher or an air-conditioning system in which UV radiation is required or is usable in an advantageous manner at a plurality of positions at a distance from one another would in each case require a corresponding number of UV sources, which, however, in view of the still high costs of UV LEDs, would disproportionately increase the outlay and would also be inefficient in many cases.

SUMMARY OF ASPECTS

Some of the aspects described below are therefore based on an object of reducing the outlay for UV disinfection that arises in the applications mentioned by way of example or in further applications. According to other or the same aspects, these may be based on an object of improving or upgrading the UV disinfection in such apparatuses operating with gases or fluids.

The object is achieved by means of an optical arrangement for disinfection in apparatuses operating with air or liquids, which optical arrangement comprises at least one radiation source or at least one group of radiation sources, which emits or jointly emit radiation in the ultraviolet wavelength range. Furthermore, the optical arrangement has at least one beam collecting optical unit, which collects the radiation emitted by the radiation source or the group of radiation sources, but also a number of beam delivering optical units, each configured to receive the radiation collected by the at least one beam collecting optical unit.

The UV radiation source can be a single UV lamp or a single UV LED. The radiation source can be an LED and a group of radiation sources can thus be a group of LEDs. The latter can in particular also be UV LEDs arranged in an array, which are provided with fixed spatial assignment and radiation alignment among one another. In the case of groups of radiation sources, the alignment need not be parallel.

According to one preferred exemplary embodiment, the radiation sources are suitable for emitting radiation in the UV-C wavelength range, for example at 254 nm (mercury line) or in the case of UV LEDs in the range between 245 nm and 285 nm, particularly preferably in an interval of 255 nm to 275 nm, since a maximum in the spectral efficacy is present in this range for many germs (bacteria, viruses, fungi and spores). According to one particularly advantageous embodiment, the UV radiation sources can be controlled in a dimmable manner in order to be able to set different power levels for the respective task in the various effect zones to be described below, and thus to ensure the highest possible efficiency. Gas discharge lamps are likewise encompassed in accordance with exemplary embodiments.

The beam collecting optical unit can comprise one or a plurality of optical elements suitable for collecting the radiation emitted by the radiation source(s) and for processing it in a beam shaping manner. The optical element(s) of the beam collecting optical unit can also be integrated into the downstream beam delivering optical unit. A main function of the beam collecting optical unit may be that of making at least one portion of the UV radiation emitted by the radiation source or the radiation sources utilizable for the use envisaged in the relevant effect zone. The beam shaping thus substantially serves for delivering the collected radiation to the beam delivering optical unit. It can have a lens, in particular a collimator lens. In accordance with one preferred embodiment, the beam collecting optical unit can have a TIR lens, particularly if a UV LED is provided as radiation source. The beam collecting optical unit can additionally have a function of homogenization with regard to the collected radiation, i.e. bring about intermixing of the collected radiation, for example. Moreover, here filtering or wavelength conversion is also possible, and in any case not excluded.

The beam delivering optical units can preferably be optical waveguides, which in the case of use are preferably formed from a UV-resistant material, for example quartz glass or UV-resistant polymer materials, etc. Alternatively or additionally, they can be optical devices such as are known for instance from the document EP 2 521 940 B1, which was filed by the present applicant and the disclosure content of which is incorporated here in its entirety, primarily the disclosure content of FIG. 1 therein with associated description. Here a carrier with a light guide consisting of lenses and mirrors is provided, which moreover is dynamically rotatable. The beam delivering optical unit can thus serve for bringing the radiation made utilizable by the beam collecting optical unit to the location of the use of the radiation optionally or proportionally in divided fashion.

Furthermore, a number of effect zones spatially separated from one another are provided, into which the radiation delivered via the beam delivering optical units is emitted in order to bring about a disinfecting effect. The respective effect depends on the apparatus and the respective region in the apparatus in which the optical arrangement is installed. All that is crucial here is that the beam delivering optical unit is configured to guide the radiation utilizable for the disinfection (sterilization) into at least two spatial zones which are at a distance spatially, and which are referred to as effect zones in this application. It should be noted that the only indirectly disinfecting effect of the UV radiation, in particular the production of ozone for subsequent introduction into the fluid (liquid or gas/air) for disinfection there, is concomitantly encompassed by the term "in order to bring about a disinfecting effect".

It should be noted that aspects of the solution proposed here also encompass the case where the radiation source(s) may already be situated at the location of one of the effect zones. In this case, under certain circumstances, an independent, separate beam delivering optical unit is not needed for the use of the UV radiation in this effect zone. Given two effect zones, for example, in this case the number of beam delivering optical units could be exactly one, i.e. one beam delivering optical unit for the spatially more distant effect zone. On the other hand, in this case, the beam collecting optical unit is already regularly coordinated with the effect zone in such a way that it performs the possibly reduced function of the beam delivering optical unit with regard to this effect zone, i.e. the respective optical elements realize both beam collecting optical unit and beam delivering optical unit.

In the case of the aspects described, it is now provided that the at least one radiation source or the at least one group of radiation sources, the at least one beam collecting optical unit and/or the number of beam delivering optical units are/is configured such that the radiation emitted by in each case a single radiation source can be delivered to at least two of the effect zones spatially separated from one another simultaneously or with a temporal spacing in each case. This affords the particular advantage that the one radiation source or the group of radiation sources can be used multiply. It is therefore no longer necessary that each effect zone and/or each point that is sensitive with regard to germ formation in an apparatus operating with fluids must be provided with a dedicated UV radiation source. Rather, the UV radiation required for the disinfection effect to be achieved is transferred from a common UV radiation source or group of radiation sources via the delivering optical units to the location of the effect zones.

As indicated above, the UV radiation can be delivered in this case simultaneously or dynamically with a temporal offset (also with a temporal overlap) or successively in the effect zones. In this case, the advantages of a dynamic adjustability of the division ratio are manifested particularly if the UV radiation is required at different points in time in the respective effect zones. In the case of a domestic appliance such as a dishwasher, for instance, it would then be possible for example (a) in a first time window to couple UV radiation into a reactor for sterilizing the washing liquor (as one example of a first effect zone),
(b) in a second time window to couple UV radiation for producing ozone into an ozone producing chamber (as one example of a second effect zone), the ozone produced subsequently being admixed with the washing liquor for an additional sterilization effect,
(c) in a third time window to guide radiation onto a surface region that is for example particularly susceptible to an accumulation of germs (as one example of a third effect zone), e.g. into a dead region in the liquid line system or into a temporary storage reservoir or pump sump, in which the liquid can stay for a relatively long time),
(d) in a fourth time window to guide UV radiation onto the washware (as one example of a fourth effect zone) itself, i.e. e.g. onto dishes, or onto laundry in the case of a washing machine,
(e) In a fifth time window, for example after the end of the dishwashing or washing process and after the removal of the washware, to guide UV radiation into the dishwashing or washing chamber (as one example of a fifth effect zone).

In this case, the individual time windows can be of different lengths and their respective temporal length can also change in the course of a complete washing process. The time windows can also overlap if beam division is configured as described below. The order of the time windows among one another can be fixed, but can also vary in the course of a complete washing process. The order can also be made dependent on the general operation of the apparatus, for example on the specific selection of the dishwashing or washing cycle.

Furthermore, the UV radiation used for the respective UV irradiation task in the individual time windows can also be chosen to be constant or can alternatively be dependent on the respective UV irradiation task or the length of the available time window. Furthermore, it is possible to use sensors such as e.g. turbidity sensors or fluorescent sensors for determining a bioburden, on the measurement of which the length of a time window or the power of the UV radiation, said power being time-dependent within the window, is made dependent. By way of example, by means of a fluorescence excitation (e.g. by means of the UV-C radiation source) and sensors that are sensitive in the UV-A, UV-B and/or visible range, the amount and possibly the type of the contamination present can be deduced. In order to avoid incorrect measurements, the sensors can be filtered with regard to the excitation light source, such that the exciting UV-C radiation is therefore not transmitted, but rather preferably reflected.

The control of the progression of the time windows and also of the UV radiation power can be carried out by a control device, which for this purpose can be connected to the respective optical elements or mechanical movement drives of the optical elements.

Overall, in the case of this aspect with its developments described, a significant advantage arises as a result of the fact that in the apparatus UV radiation can be used in a targeted manner where it is required or can be used at least in a supporting manner, while no further costly radiation sources need be implemented for this purpose. Costs and complexity can thus be reduced and the flexibility of the UV disinfection can be increased.

According to one development of the optical arrangement, the apparatus, as already indicated in the introduction, can be a washing machine or a dishwasher, or alternatively a ventilation and air-conditioning system, in particular an air-conditioning system, a ventilation system, an air circulation system, an air dehumidifier or an air humidifier. In these cases, a plurality of sensitive points with regard to germ formation can regularly be identified, such that the optical arrangement proposed here in accordance with specific embodiments can be used advantageously.

According to a further development of the optical arrangement, a number of at least two beam collecting optical units are provided. In this case, the at least one radiation source or the at least one group of radiation sources is configured as movable between the beam collecting optical units, such that depending on a selection of an effect zone to be disinfected the at least one radiation source or the at least one group of radiation sources can interact with one of the beam collecting optical units. In other words, the at least one radiation source or the at least one group of radiation sources can optionally be moved from one of the beam collecting optical units to another. There is preferably a predefined assignment between the beam collecting optical units and the beam delivering optical units, such that each of the beam collecting optical units that can be moved to can ultimately correspond to one of the effect zones.

The moving to one of the beam collecting optical units by the radiation source can then thus correspond to a UV disinfection in the selected effect zone. In this case, the movability of the radiation source or of the at least one group of radiation sources can include the respective adoption of a specific position vis-à-vis an optical element of the beam collecting optical unit in order to ensure that at least a large portion of the UV radiation is collected. This arrangement allows the optical elements of the beam collecting optical unit and also of the beam delivering optical units to be fixedly installed, such that for example a misalignment thereof over long periods of operation can be avoided. At the same time only one movement of the radiation source(s) is required. In the case of LEDs the outlay here is particularly low.

According to one development of the optical arrangement described in the previous paragraph, the at least one radiation source or the at least one group of radiation sources is mounted on a movable mount. The latter can be moved e.g. by an electric motor operated by a control device. The mount can preferably be translationally displaced or rotated in a plane substantially perpendicular to an optical axis of the beam collecting optical unit. This enables a geometrically relatively simple set-up of the beam collecting optical units next to one another.

According to one development of the optical arrangement as an alternative to that, the at least one radiation source or the at least one group of radiation sources is likewise mounted on a movable mount, which can be rotated in a plane. Here, however, the plane includes the optical axis of the beam collecting optical units, or in other words: the rotation axis of the mount is perpendicular to the optical axis of the beam collecting optical unit. The same advantage as in the case of the development in the previous paragraph is achieved analogously here. Only one movement is required in order to bring about a change of the irradiation from one effect zone to the next.

According to further developments of the optical arrangement, only a single radiation source or a single group of radiation sources is provided, which is now faced with a number of at least two beam collecting optical units. The beam collecting optical units are configured as movable in relation to the radiation source or the group of radiation sources in order optionally, depending on a position that they adopt on account of the movement, to collect the radiation emitted by the radiation source or the group of radiation sources. Two aspects are suitable:

Only one beam delivering optical unit and only one effect zone assigned to this beam delivering optical unit are configured. Depending on a selection of one of the beam collecting optical units for a position in which it can collect the radiation emitted by the radiation source or the group of radiation sources, via the beam delivering optical unit, a radiation distribution in the effect zone is then adjustable.

Alternatively, a number of beam delivering optical units and a corresponding number of effect zones assigned thereto can be provided, wherein each of the beam collecting optical units is assigned to exactly one of the beam delivering optical units and effect zones in order to deliver the collected radiation to only one relevant effect zone optionally depending on the position relative to the radiation source.

In both of these aspects it is the beam collecting optical units that are movable relative to the radiation source or the group of radiation sources. By moving the beam collecting optical units relative to the radiation source or the group of radiation sources, it is possible to make a selection as to which of the beam collecting optical units is intended subsequently to collect and pass on the radiation. In the first of the two aspects, the selection of the beam collecting optical unit is simply utilized only to achieve a desired radiation distribution in the only one single effect zone. In the case of the second aspect, the selection of one of the beam collecting optical units is associated with the selection of an effect zone. These aspects make it possible to exploit the fact that the radiation source(s) as electronic components need not be moved, with the result that the set-up becomes simpler overall.

According to further developments of the optical arrangement, the at least one radiation source or the at least one group of radiation sources is assigned in each case to a beam collecting optical unit and together with the latter forms a unit. The unit comprising the at least one radiation source or the at least one group of radiation sources and the respective beam collecting optical unit, on a common mount, is configured as movable between the beam delivering optical units, such that depending on a selection of an effect zone to be disinfected the unit can interact with one of the beam delivering optical units. This embodiment exploits the fact that the mutual positioning of radiation source(s) and beam collecting optical unit can be configured mechanically stably since mutual movement is not required. As a result, the set-up is simplified overall and the beam collecting accuracy and hence the quality of the selected radiation distribution in the effect zone are improved.

In accordance with a further development, the optical arrangement can furthermore comprise a radiation divider, which divides the radiation collected by the at least one beam collecting optical unit into radiation portions and is configured to selectively deliver the radiation portions to in each case one of the beam delivering units. In other words, the beam divider splits the radiation into different portions. As a result, suitable and respectively appropriate radiation distributions can be realized in the effect zones. In particular, a simultaneous delivery of radiation portions into the effect zones is also possible if this is required for example at the same point in time for disinfection purposes in accordance with a program sequence (e.g. dishwasher, etc.).

The following elements, for example, can be used as radiation dividers or radiation splitters or radiation distributors: electrochromic mirrors, movable mirrors with a transmission region and a reflection region (e.g. translation, rotation), tiltable mirrors: single mirror or array of mirrors (e.g. DMD), movable lenses (e.g. translation, tilting), movable glass wedges (e.g. translation, rotation), movable optical components tilted with respect to the incident beam, e.g. plane-parallel plates, diffusing plates, microlens array (e.g. translation, rotation), etc., movable fiber bundles (e.g. turret arrangement).

One development of this aspect provides for the radiation divider to be configured as adjustable in order to be able to adapt the radiation portions in each case. As a result, the radiation portions can be adjusted in a temporally variable manner.

One development of this aspect provides for the radiation divider to be an in particular translationally movably configured mirror, which, depending on a degree of overlap with the radiation collected by the beam collecting optical unit and delivered, couples out a first radiation portion and delivers it to a first beam delivering unit and does not couple out a second radiation portion and thereby delivers it to a second beam delivering unit.

According to another embodiment of the optical arrangement proposed here, the latter comprises an in particular rotatably configured mirror, which, depending on a tilting, delivers the radiation collected by the beam collecting optical unit optionally to one of the beam delivering units. The mirror can deflect the radiation in a desired direction to a beam delivering optical unit and thus switch between the effect zones. This aspect is suitable particularly in the case of a temporally successive application of the UV radiation in the different effect zones.

In one simple embodiment, the movable mirror can be a plane movable reflector. It can also be concave or convex in order to achieve a focusing or defocusing effect. Moreover, it can be identical with the beam delivering optical unit if it itself bridges the optical distance to the effect zone. According to an alternative embodiment, however, said mirror can also be a hollow-cylinder-segment-shaped mirror configured as rotatable about its center axis, which mirror simultaneously forms the beam collecting optical unit in relation to the radiation source and also the beam delivering optical unit assigned to the beam collecting optical unit, wherein the radiation source preferably itself emits radiation in a full circle of 360° in a plane perpendicular to the center axis. A particular advantage arises here if the radiation source(s) is (or are) situated within the hollow cylinder formed by the mirror and said hollow cylinder effects a rotational movement around the radiation source(s). As a result, a particularly large portion of the radiation can be collected and then directed in the direction of a specific selected effect zone. One exemplary case can concern a radiation source (or a group of radiation sources) which emits radiation in a full circle (360°), or into the full solid angle.

According to embodiments of all the aspects mentioned above, the at least one beam collecting optical unit can be a TIR lens (TIR: total internal reflection). Such lenses have a fitting shape designed e.g. for encapsulated LEDs. They allow a high degree of optical coupling and can be manufactured from PMMA, silicone or glass, for example, without restricting the generality, with the temperatures and the wavelength range that they are intended to withstand playing a part in the choice of material. TIR lenses are particularly suitable in the present case because they can make a considerable contribution to the homogenization of the collected radiation (collimated or extremely focused radiation), in comparison for instance with a case in which a conventional hollow reflector mirror or a conventional lens is used.

Furthermore, in embodiments in accordance with all the aspects mentioned above, the beam delivering optical units can be represented by optical waveguides or beam paths defined by lens and/or mirror arrangements including combinations thereof. With optical waveguides, even relatively large distances between radiation source(s) and effect zones can be overcome with only very low power losses.

With regard to beam paths defined by lens and/or mirror arrangements including combinations thereof, movable or adjustable arrangements as described above with reference to the document EP 2 521 940 B1 are also encompassed. Particularly by means of such arrangements, too, relatively large distances between radiation source(s) and effect zones can be overcome with only very low power losses.

Moreover, according to embodiments of all the aspects mentioned above, the effect zones, in the apparatuses, can be containers forming UV reactors, surfaces of mounts, pump sumps, interior walls of washing appliances, outlets, heat exchangers and/or water or air filters.

Further advantages, features and details of the invention are evident from the claims, the following description of preferred embodiments and also with reference to the drawings. In the figures, identical reference signs designate identical features and functions.

BRIEF DESCRIPTION OF THE DRAWING(S)

Figure 1:
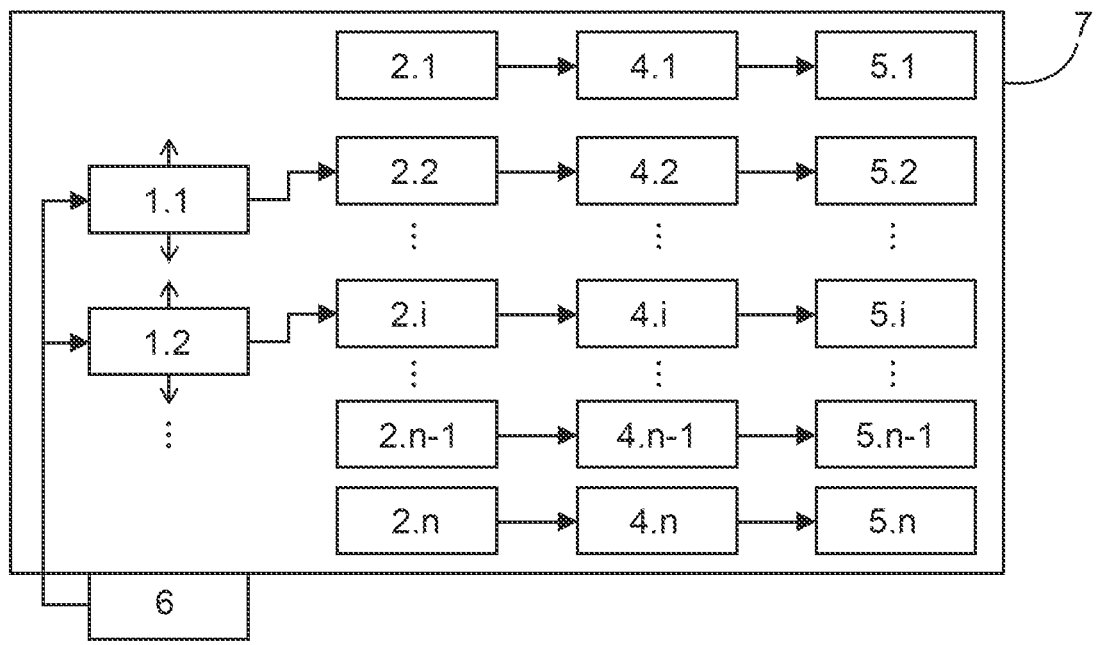
FIG. 1 shows in a schematic diagram one embodiment of an optical arrangement for disinfection in an apparatus operating with air or a liquid, wherein a radiation source or a group of radiation sources is configured as movable between a number of beam collecting optical units.
Figure 4A:
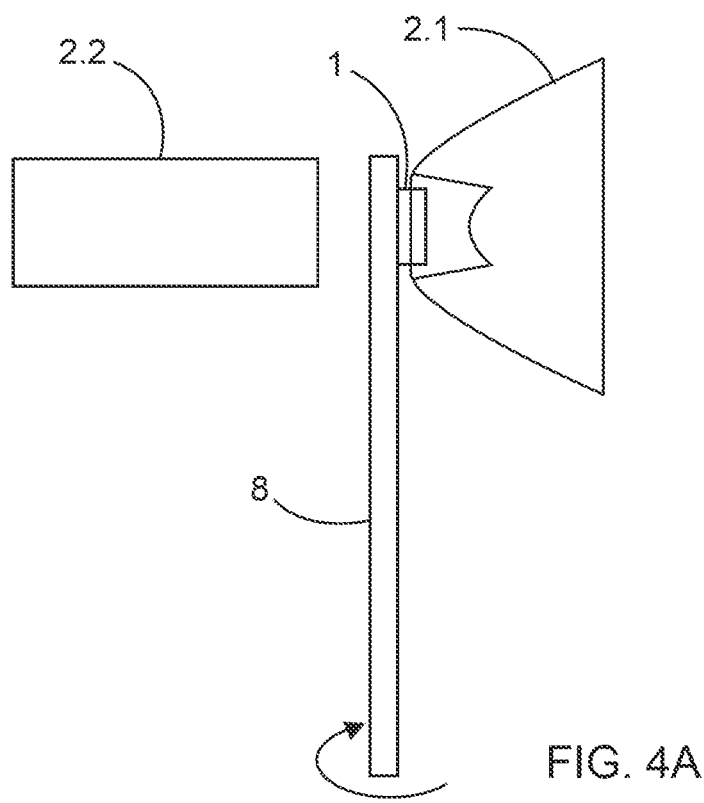
Figure 4B:
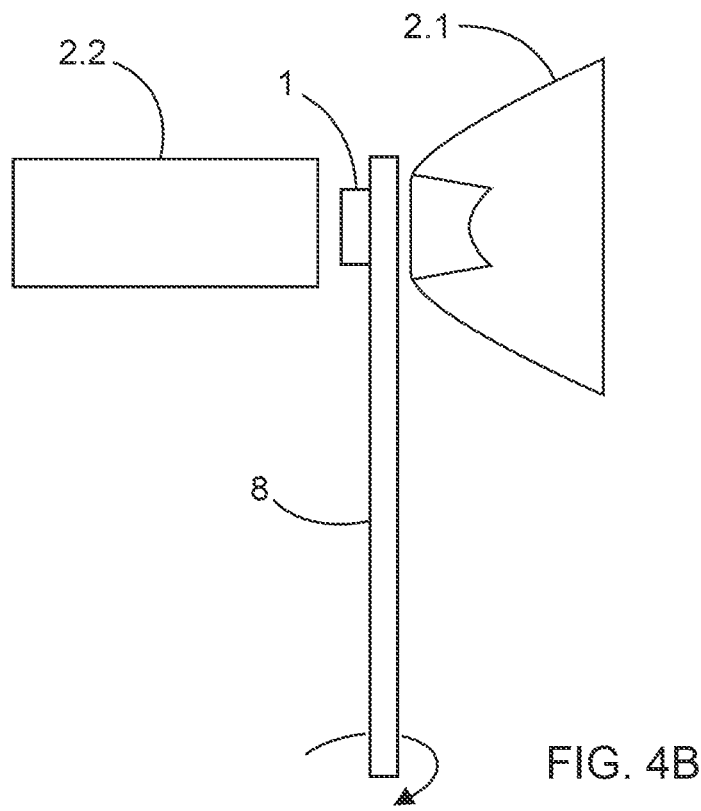
Figure 5A:
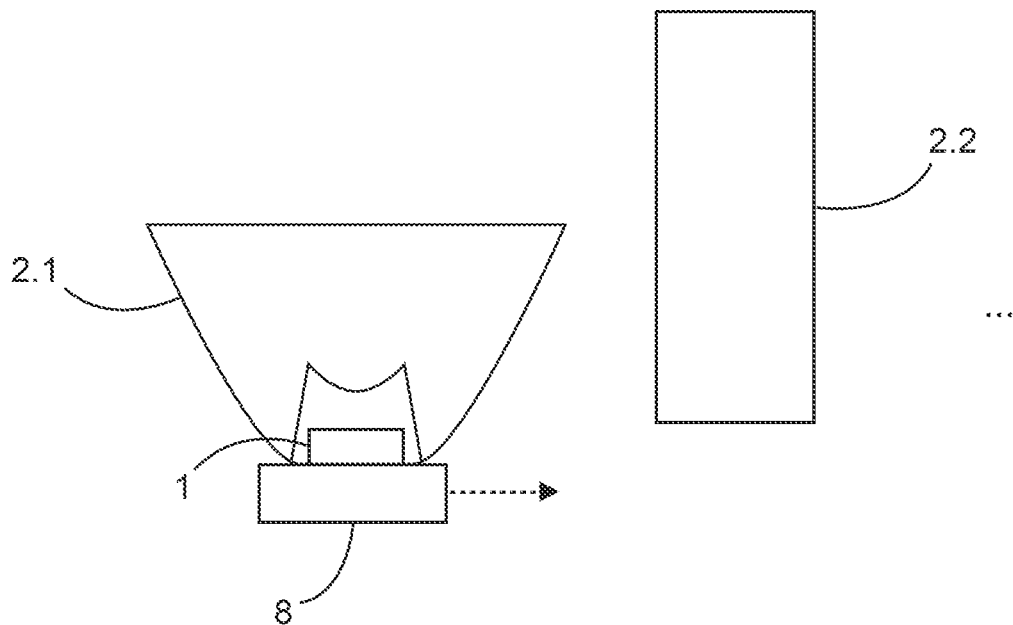
Figure 5B:
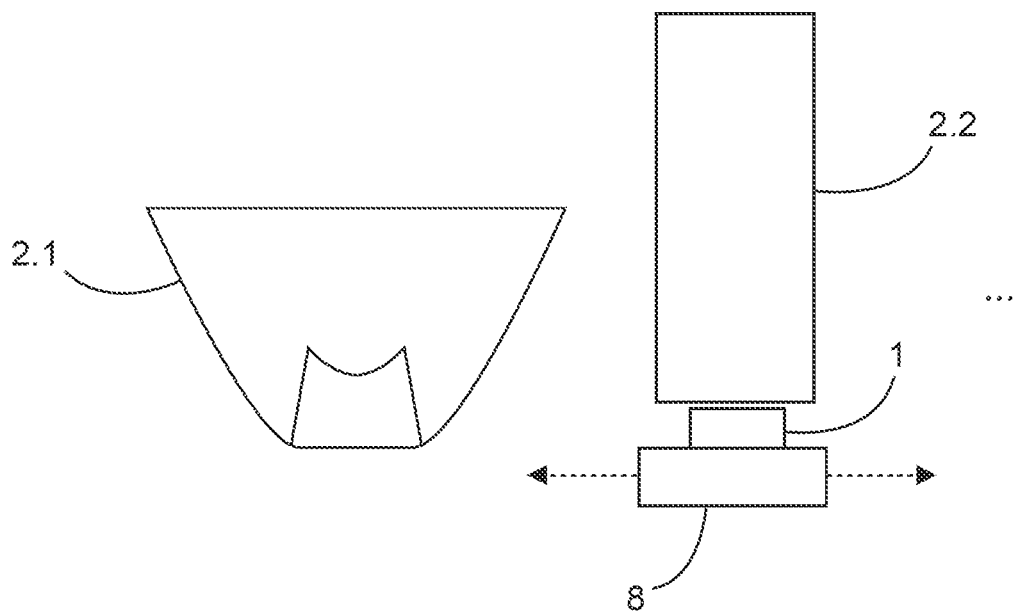
Figure 6:
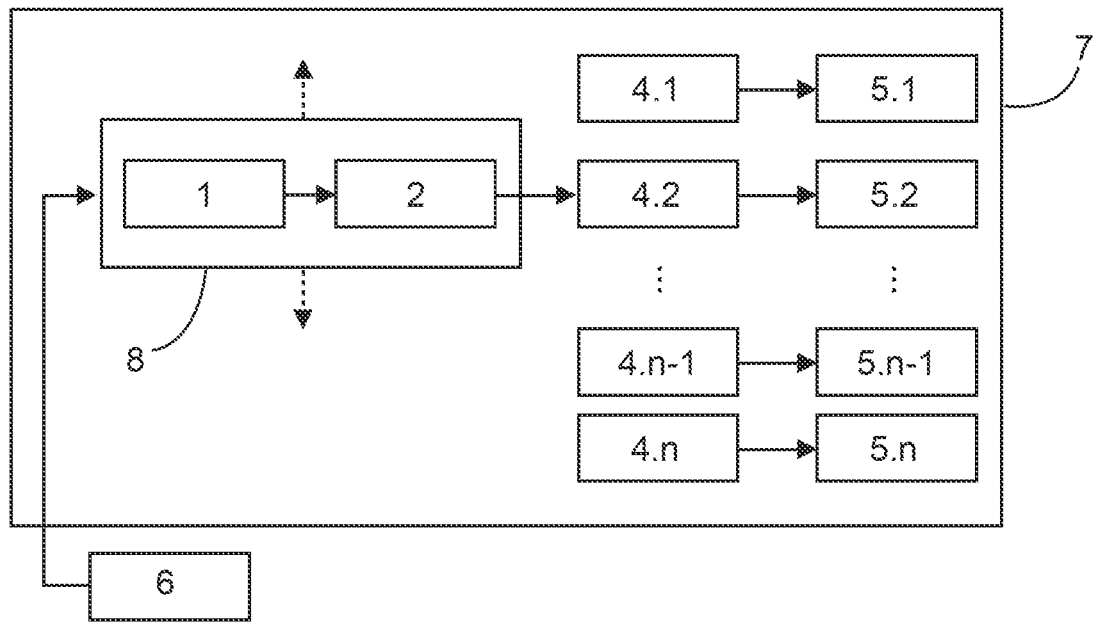
Figure 7:
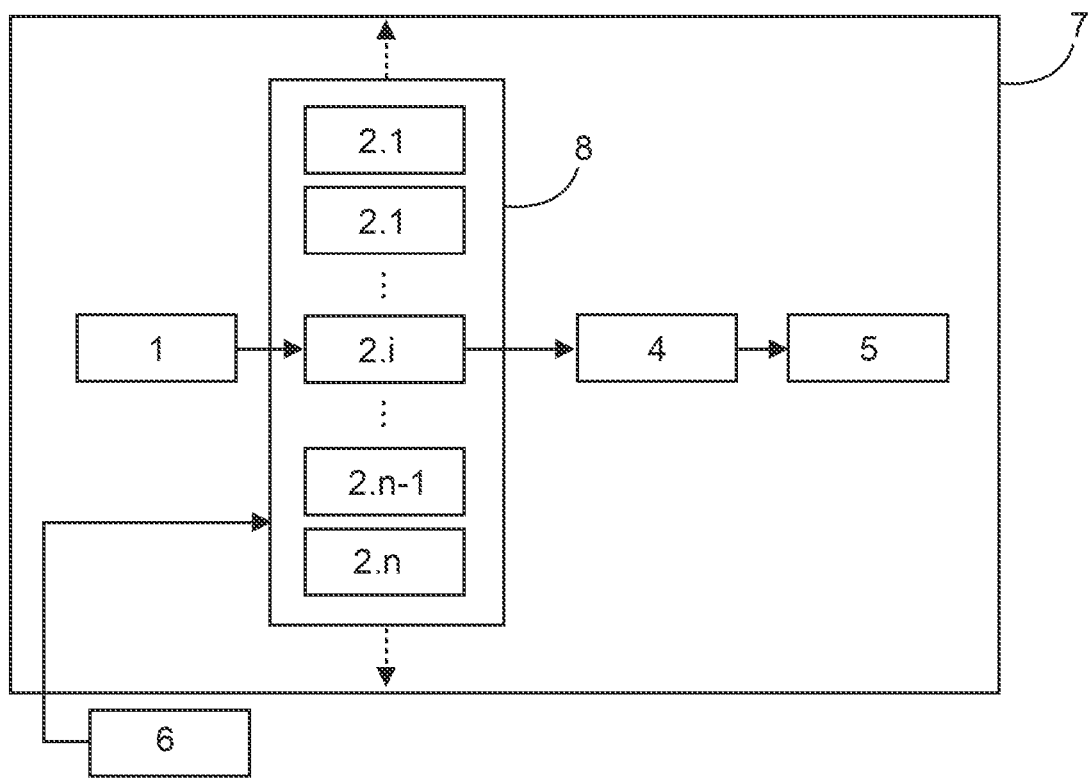
Figure 8:
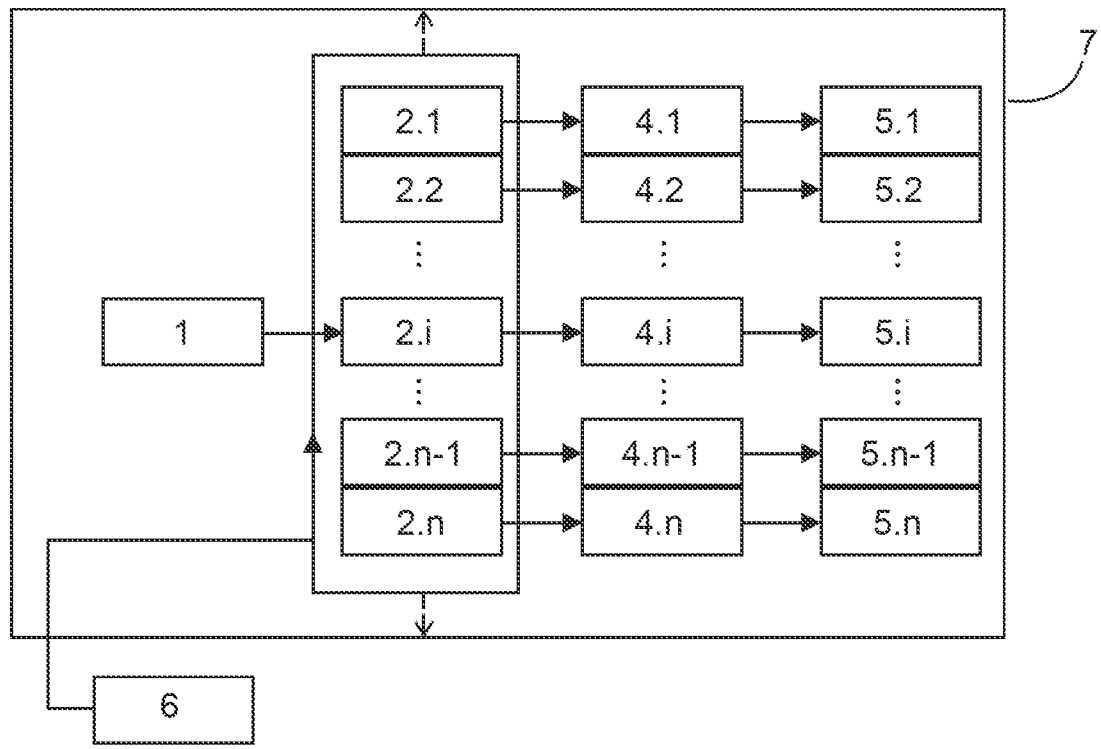
Figure 9:
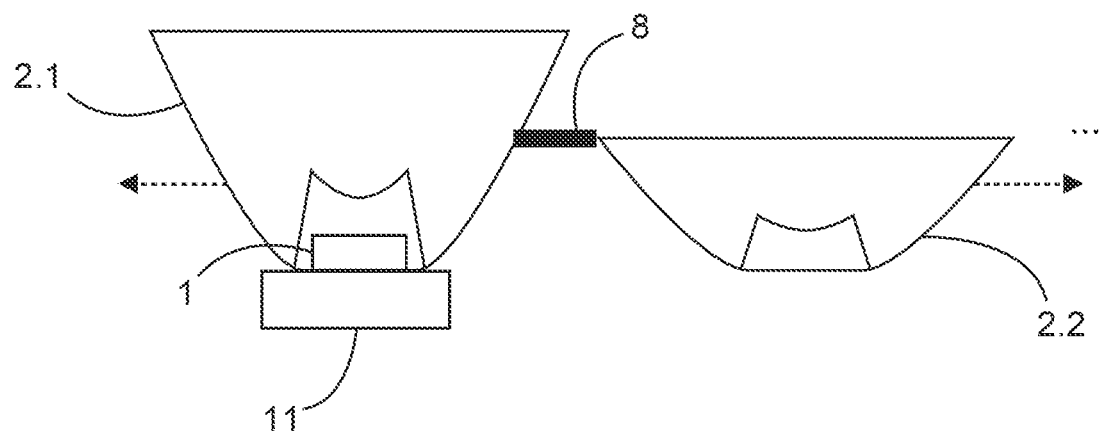
Figure 10:
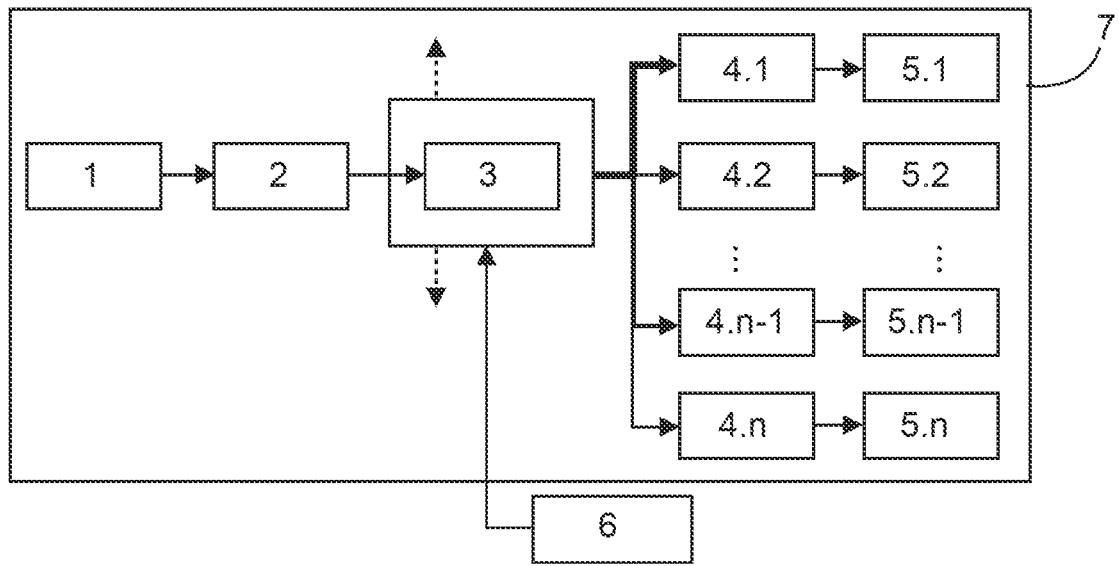
Figure 11:
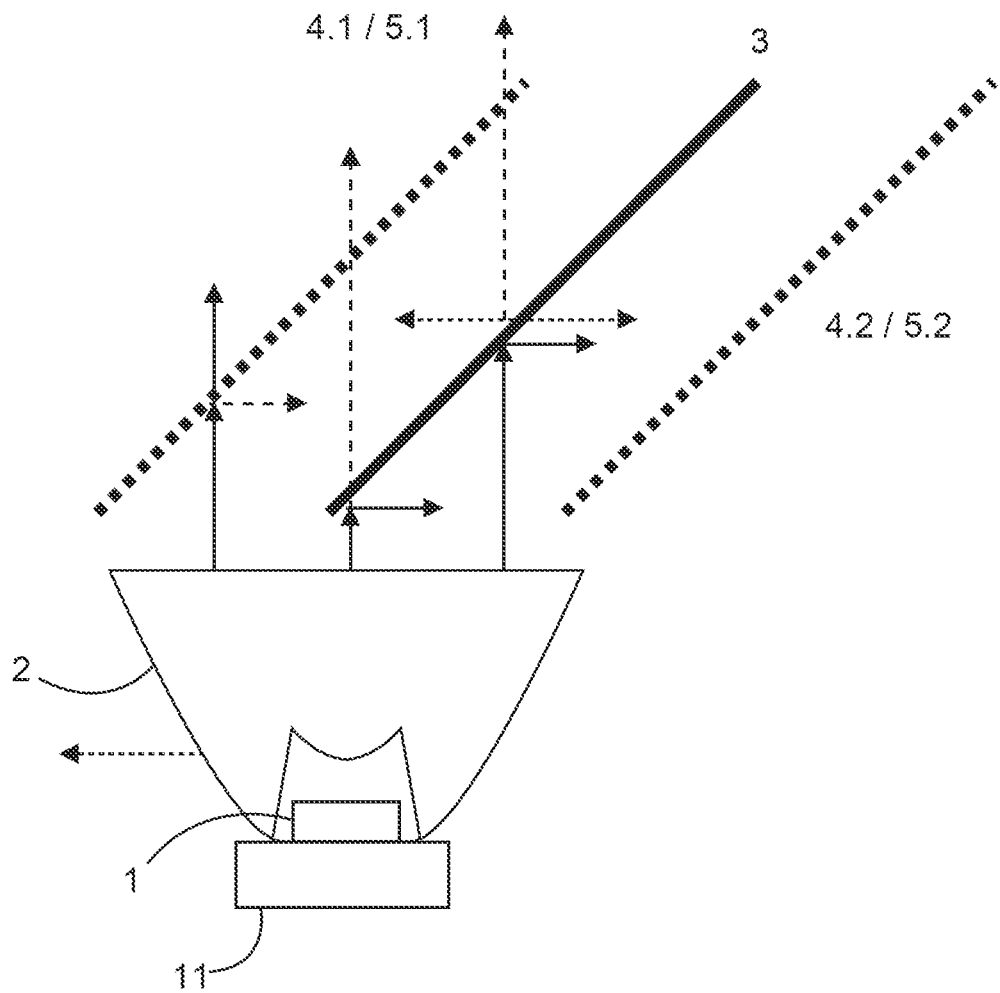
Figure 12:
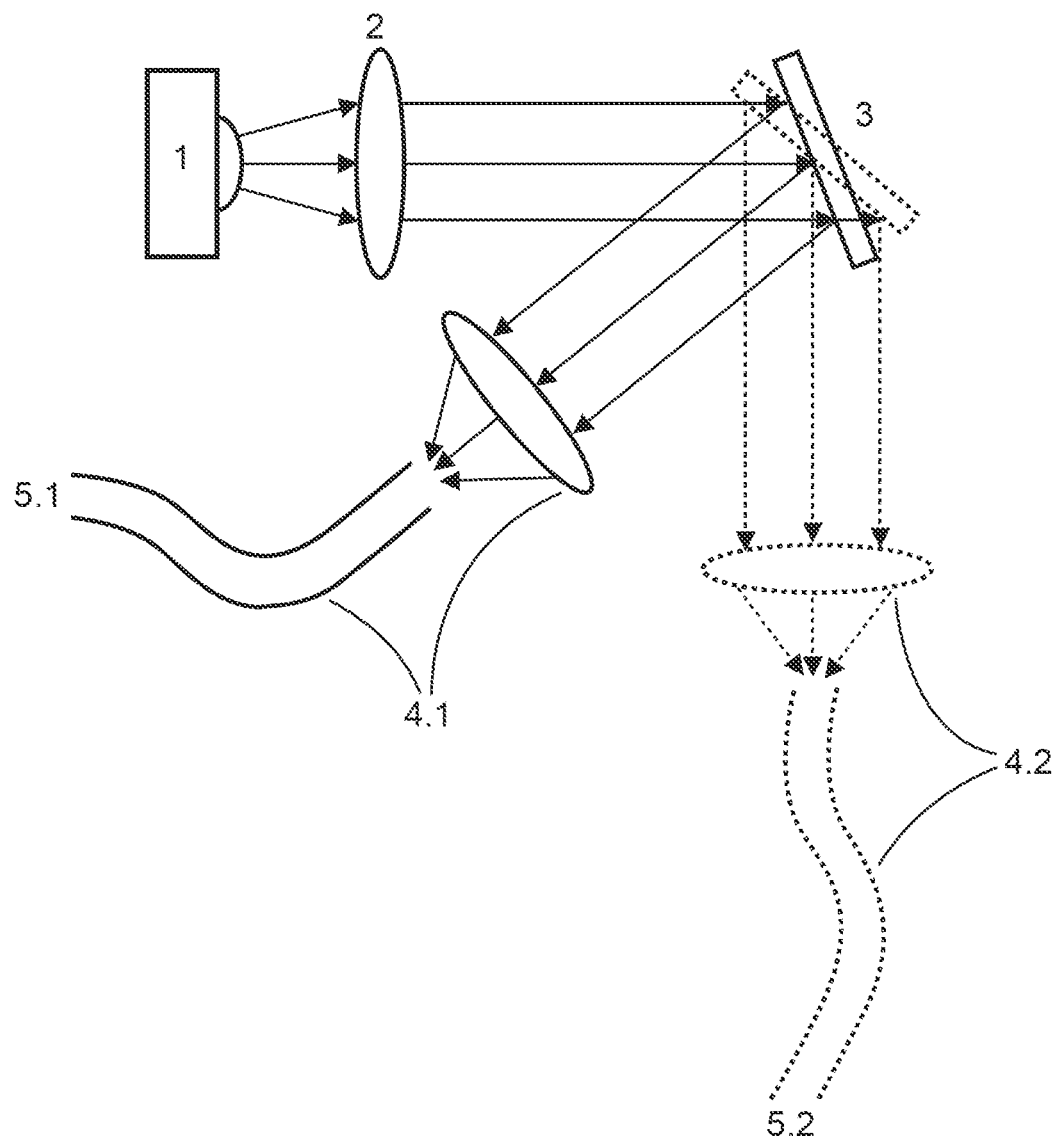
Figure 13A:
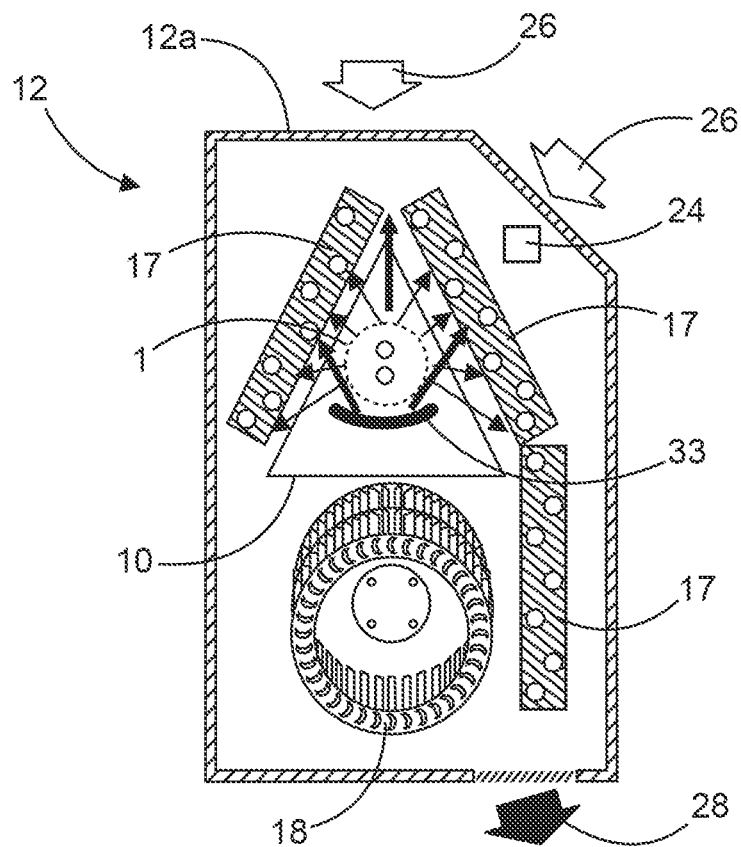
Figure 13B:
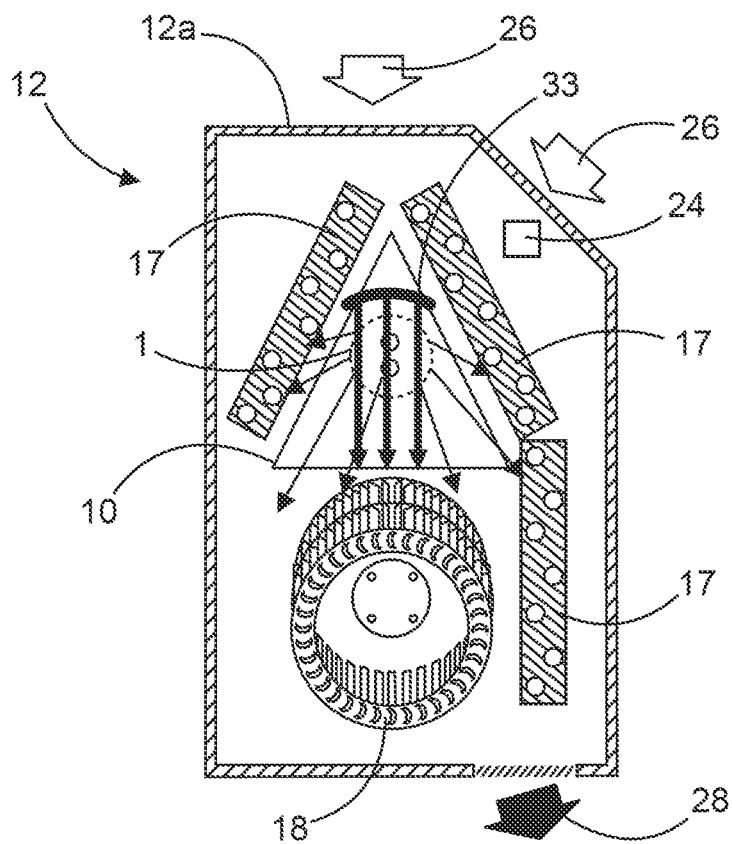

FIG. 4A shows an optical arrangement as in FIG. 1 in a schematic side view in accordance with a third exemplary embodiment, wherein the radiation source(s) is (are) mounted on a movable mount, which can be rotated about a rotation axis perpendicular to the optical axis of here two beam collecting optical units, wherein the radiation source(s) face(s) one of the beam collecting optical units in a first state;

FIG. 4B shows the optical arrangement from FIG. 4A, wherein the radiation source(s) face(s) the other beam collecting optical unit in a second state;

FIG. 5A shows an optical arrangement as in FIG. 1 in a schematic side view in accordance with a fourth exemplary embodiment, wherein the radiation source(s) is (are) mounted on a movable mount, which can be translationally displaced in a direction perpendicular to an optical axis of two beam collecting optical units, wherein the radiation source(s) face(s) one of the two beam collecting optical units in a first state;

FIG. 5B shows the optical arrangement from FIG. 5A, wherein the radiation source(s) face(s) the other beam collecting optical unit in a second state;

FIG. 6 shows in a schematic diagram a further embodiment of an optical arrangement for disinfection in an apparatus operating with air or a liquid, wherein the radiation source(s) and the beam collecting optical unit(s) as a unit on a common mount are configured as movable between a number of beam delivering optical units;

FIG. 7 shows in a schematic diagram a further embodiment of an optical arrangement for disinfection in an apparatus operating with air or a liquid, wherein a number of beam collecting optical units are configured as movable both relative to the radiation source(s) and relative to a beam delivering optical unit;

FIG. 8 shows in a schematic diagram a further embodiment of an optical arrangement for disinfection in an apparatus operating with air or a liquid similar to that in FIG. 7, wherein however the number of beam collecting optical units are configured as movable relative to a multiplicity of beam delivering optical units;

FIG. 9 shows an optical arrangement as in FIG. 8 in a schematic side view in accordance with a fifth exemplary embodiment, wherein two beam collecting optical units are mounted on a common mount and connected to one another, said common mount being configured as movable relative to the radiation source(s);

FIG. 10 shows in a schematic diagram a further embodiment of an optical arrangement for disinfection in an apparatus operating with air or a liquid, wherein a radiation divider is provided, which divides radiation into radiation portions and is configured to selectively deliver the radiation portions to in each case one of the beam delivering optical units;

FIG. 11 shows an optical arrangement as in FIG. 10 in a schematic side view in accordance with a sixth exemplary embodiment, wherein the radiation divider is a translationally movably configured mirror, which, depending on a degree of overlap with the radiation collected by the beam collecting optical unit and delivered, couples out radiation portions and correspondingly delivers them to the beam delivering optical units;

FIG. 12 shows an optical arrangement according to a principle similar to that in FIG. 10 in a schematic side view in accordance with a seventh exemplary embodiment, wherein a rotatably configured mirror is provided, which depending on a tilting, delivers the radiation collected by the beam collecting optical unit optionally to one of the beam delivering optical units;

FIG. 13A shows an optical arrangement according to a principle similar to that in FIG. 10 in a schematic side view in accordance with an eighth exemplary embodiment, wherein a hollow-cylinder-segment-shaped mirror configured as rotatable about its center axis is provided, which in a first position partly collects, deflects and delivers to a first effect zone the radiation emitted by the radiation source in a plane perpendicular to the center axis in a full circle of 360°;

FIG. 13B shows the optical arrangement from FIG. 13A, wherein the mirror in a second position partly collects, deflects and delivers to a second effect zone the radiation emitted by the radiation source in a plane perpendicular to the center axis in a full circle of 360°.

In the following description of preferred exemplary embodiments, it should be taken into account that the present disclosure of the various aspects is not restricted to the details of the set-up and arrangement of the components such as are presented in the following description and in the figures. The exemplary embodiments can be implemented or embodied in various ways in practice. It should furthermore be taken into account that the mode of expression and terminology used here are used merely for the purpose of concrete description and they should not be interpreted in a restrictive manner as such by the person skilled in the art.

Firstly, various exemplary embodiments in accordance with a first fundamental embodiment illustrated schematically in FIG. 1 will be explained with reference to FIGS. 2A to 5B. Referring to FIG. 1, an apparatus 7, which can be for example a washing machine, a dishwasher or a ventilation and air-conditioning system, in particular an air-conditioning system, a ventilation system, an air circulation system, an air dehumidifier or an air humidifier, has an optical arrangement for disinfection of a liquid or of air with which the apparatus 7 operates, or of surfaces at sensitive points present therein.

The optical arrangement comprises UV radiation sources 1.1 and 1.2 (the number thereof is not limited to the two radiation sources shown in FIG. 1—according to one modification, it is also possible for just a single UV radiation source 1.1 to be provided), which emit radiation in the ultraviolet wavelength range. The UV radiation sources 1.1 and 1.2 can also each be a plurality of radiation sources, i.e. groups of radiation sources. The UV radiation sources 1.1 and 1.2 can comprise UV LEDs, in particular ones which emit UV radiation in the range—particularly effective vis-à-vis bacteria on biofilms—of 249 nm to 338 nm, preferably in the wavelength range of 292 nm to 306 nm, or else preferably in the range of 245 nm to 285 nm, in particular 255 nm to 275 nm. The UV radiation sources can have different properties, such as e.g. different wavelengths, dimensions, powers, etc. If at least one UV radiation source 1.1 or 1.2 etc. comprises a group of radiation sources, then different wavelengths can be provided within the group as well.

Furthermore, the group has a number of beam collecting optical units 2.1-2.$n$ (here n denotes an arbitrary number). The latter collect the radiation emitted by the UV radiation sources 1.1 and 1.2. This includes the case where only a portion of the radiation can be collected. The beam collecting optical units 2.1-2.$n$ are adapted for the respective tasks in the effect zones to be described below and are respectively assigned to a beam delivering optical unit 4.1-4.$n$, each configured to receive the radiation collected by the respective beam collecting optical unit 2.1-2.$n$. In this embodiment and also in all embodiments described below, the beam collecting optical units 2.1-2.$n$ have the function of making the emitted UV radiation utilizable by virtue of the fact that they collect the largest possible portion thereof and preferably also process it further, for example homogenize, collimate or focus it, in order to deliver it in a suitable manner to the respective beam delivering optical unit 4.1-4.$n$, for example by coupling into an optical waveguide, etc., and/or to bring about a suitable radiation distribution in the effect zone. The beam delivering optical units 4.1-4.$n$ can have a function of providing the radiation received by them across a distance in the apparatus 7 at the location of use, i.e. in the effect zones 5.1-5.$n$.

The effect zones 5.1-5.$n$ are respectively assigned to one of the beam delivering optical units 4.1-4.$n$. In this first fundamental embodiment, they are generally present in the same number as the beam collecting optical units 2.1-2.$n$ and the beam delivering optical units 4.1-4.$n$. In this embodiment, the beam collecting optical units 2.1-2.$n$, the beam delivering optical units 4.1-4.$n$ and the effect zones 5.1-5.$n$ in each case form a beam guiding sequence. The effect zones 5.1-5.$n$ are spatially separated from one another in the apparatus. The effect zones 5.1-5.$n$ denote locations, surfaces or spaces in the apparatus 7 in which a disinfecting effect is brought about. These locations, surfaces or spaces in the apparatus 7 can be sensitive points with regard to the arising of germs or biofilms.

In the first fundamental embodiment, at least one (preferably all) of the UV radiation sources 1.1 or 1.2 etc. is configured as movable, as is indicated schematically in FIG. 1. In this case, the UV radiation sources 1.1 and 1.2 (etc.) can move between the beam collecting optical units 2.1-2.$n$, or more precisely: they can be moved to the different ports or the input coupling surfaces of the respective beam collecting optical units 2.1-2.$n$, e.g. by translation or rotation. In this case, a port should be understood to mean a position relative to the respective input coupling surface of the relevant beam collecting optical unit 2.1-2.$n$ in which an optimum beam collecting yield is achieved, or a position of the radiation source in which a desired homogenization is achieved, such as, for instance, a focal point, etc. If a beam collecting optical unit 2.1-2.$n$ is e.g. a TIR lens, then a fitting shape recess for e.g. encapsulated LEDs is regularly provided therein. The corresponding movement position constitutes such a port. The UV radiation sources 1.1 and 1.2 can in each case (optionally including substrate on which they can be mounted) be mounted on mounts (not illustrated in FIG. 1) configured as movable.

The movability of the UV radiation sources 1.1 and 1.2 etc. can be realized by rails and/or arms and joints etc. The drive can be effected by an electric motor, by piezoelements or the like, which is/are part of a control device 6 indicated in FIG. 1, which can itself be a separate component or part of a superordinate control device of the apparatus 7, in order to realize the temporal sequence of the disinfection or of the irradiation depending on the operation and state of the apparatus 7.

Figure 2A:
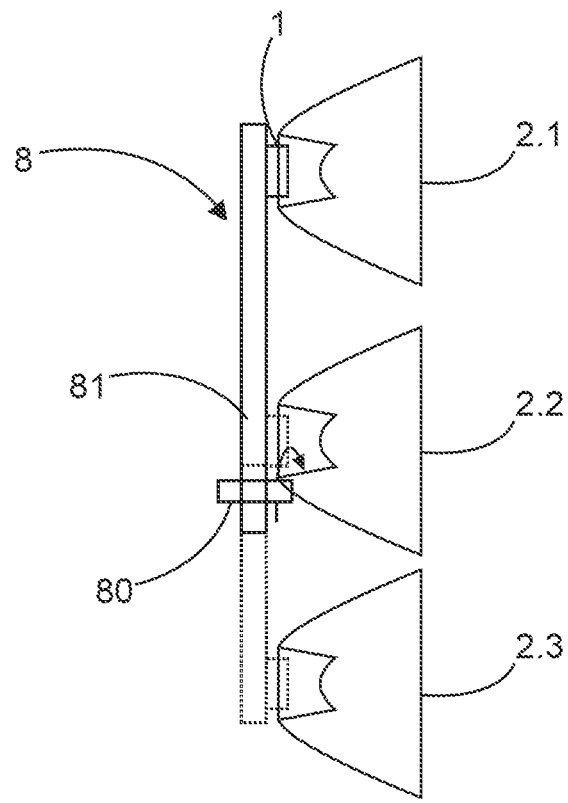
FIG. 2A shows an optical arrangement as in FIG. 1 in a schematic side view in accordance with a first exemplary embodiment, wherein the radiation source(s) is (are) mounted on a movable mount, which can be rotated in a plane substantially perpendicular to an optical axis of here three beam collecting optical units.
Figure 2B:
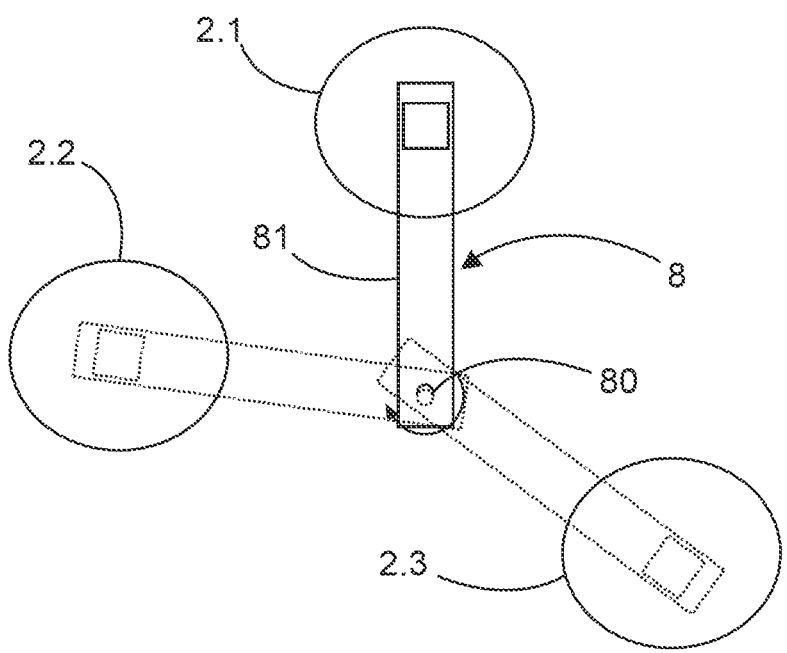
FIG. 2B shows the optical arrangement from FIG. 2A, but in a plan view.

With respect to the embodiment illustrated in FIG. 1, FIGS. 2A and 2B then show a first concrete exemplary embodiment. FIG. 2A shows a side view and FIG. 2B the corresponding plan view of an optical arrangement. The latter has an LED as UV radiation source 1, which is mounted on an arm 81 rotatable about a rotation axis 80. The arm 81 can be or comprise a circuit board, on which the LED is mounted. In this case, the LED (UV radiation source 1) is positioned at a distance from the rotation axis 80, such that the LED in the case of rotation described a circular movement with the radius of the distance. The orientation of the LED is such that a main emission direction of LED points parallel to the rotation axis 80. The rotatable arm 81 forms a movable or here rotatable mount for the radiation sources.

Furthermore, the optical arrangement in FIGS. 2A and 2B comprises three beam collecting optical units 2.1, 2.2 and 2.3 embodied as TIR lenses. The spatial position and orientation of the beam collecting optical units 2.1, 2.2 and 2.3 as well as those of the rotation axis 80 are fixedly predefined (substantially immovable). The optical axes of the three beam collecting optical units 2.1, 2.2 and 2.3 are parallel to one another and also parallel to the rotation axis 80. The TIR lenses have fitting shape recesses for accommodating the LED, such that the radiation emitted by it can be optimally coupled into the TIR lens in order for example to have a homogenizing effect on the radiation. These positions in the fitting shape recesses constitute ports for the movement of the UV radiation source 1. In this case, the beam collecting optical units 2.1, 2.2 and 2.3 are positioned such that their optical axes lie on the radius of the circular movement of the UV radiation source 1. This results in three angular positions which correspond to the beam collecting optical units 2.1, 2.2 and 2.3 and into which the arm 81 with the UV radiation source 1 can be moved by driving by the control device 6 (see FIG. 1) in order to select one of the beam collecting optical units 2.1, 2.2 and 2.3 and thus an effect zone 5.1, 5.2, or 5.3 assigned to it (see FIG. 1).

In order to be able to accommodate the LED in the context of a movement into the fitting shape recess of a TIR lens, the optical unit or the LED can be moved in an additional step for example such that there is no longer any contact during the translation/rotation, or the optical element itself has a corresponding cutout through which the LED passes without contact during the translation/rotation. In the second case, it may be necessary to accept reductions in terms of the collection efficiency for the radiation, but they may be perfectly acceptable.

Optional beam dividers, delivering optical units (e.g. mirror arrangements such as, for instance, free-space optical units or optical waveguides) and effect zones are not explicitly illustrated in FIGS. 2A and 2B, but in this regard reference can be made to the analogous set-up of exemplary embodiments described below. It should be noted that an additional beam divider 3 can also be provided for one or more of the beam collecting optical units 2.1 to 2.3, such that a beam collecting optical unit supplies two or more effect zones with UV radiation. This also applies to the following or previous exemplary embodiments. Furthermore, further LEDs (not illustrated in FIGS. 2A and 2B) can also be moved to the various ports by means of a corresponding movement. This likewise applies to the subsequent exemplary embodiments as well.

Figure 3:
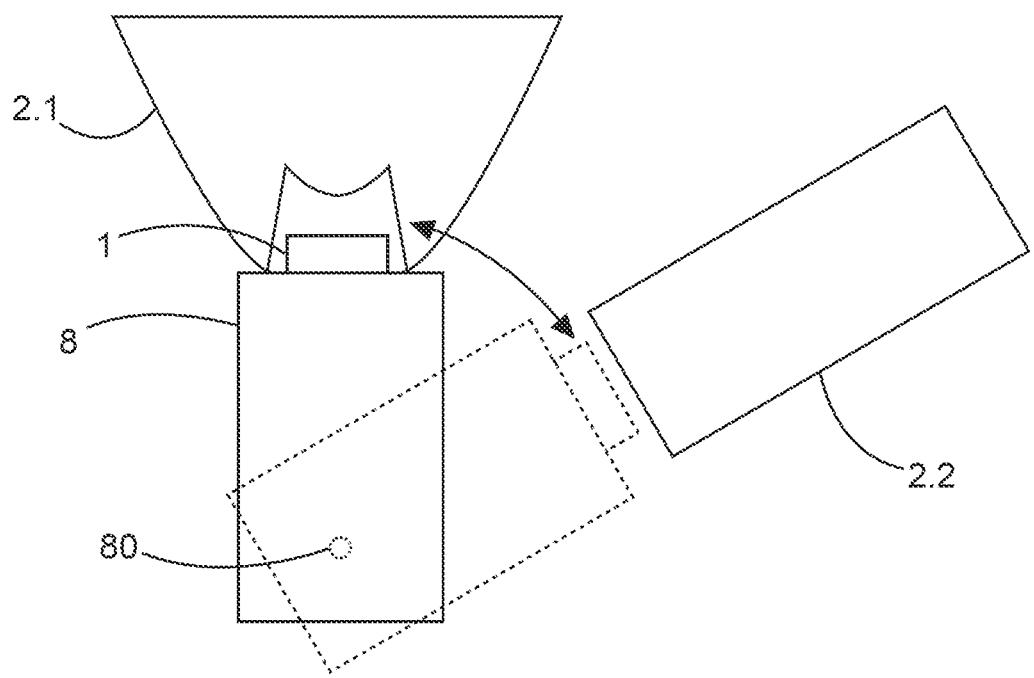
FIG. 3 shows an optical arrangement as in FIG. 1 in a schematic side view in accordance with a second exemplary embodiment, wherein the radiation source(s) is (are) mounted on a movable mount, which can be rotated about a rotation axis perpendicular to the optical axis of here two beam collecting optical units.

FIG. 3 shows a second exemplary embodiment, in which an LED as UV radiation source 1 is mounted on a rotatable mount 8. The mount 8 is configured as rotatable about a rotation axis 80 and can be moved in rotary fashion between two positions or ports for the UV radiation source 1 by the control device 6 (see FIG. 1), such that a first beam collecting optical unit 2.1 embodied as a TIR lens and respectively a second beam collecting optical unit 2.2 embodied as a glass rod can optionally receive (at least partly) the UV radiation emitted by it. The TIR lens collimates the radiation, while the glass rod, by means of multiple total internal reflection, mixes the radiation, and in the process homogenizes and transports it. The glass rod can be embodied in quite varied ways: conical or CPC (compound parabolic concentrator), wherein it then also has a collimating function, and/or it has a round, rectangular, hexagonal cross section or the like.

Here, too, the beam collecting optical units 2.1 and 2.2 are mounted substantially in a stationary manner and have optical axes that are perpendicular to the rotation axis 81 of the mount and point away from it. The main emission direction of the LED, too, is perpendicular to the rotation axis 81, points away from it and is brought in line with the respective optical axis of the beam collecting optical unit 2.1 or 2.2 by means of the optional movement to the ports by means of the control device 6. The exemplary embodiment is not restricted to two beam collecting optical units; further beam collecting optical units can be provided. As in the first exemplary embodiment, beam delivering optical units such as e.g. mirror arrangements with a free-space optical unit or optical waveguide, effect zones and optionally also beam dividers can be provided.

FIGS. 4A and 4B show a third exemplary embodiment of an optical arrangement based on FIG. 1. The set-up is very similar to that in the second exemplary embodiment. However, in the third exemplary embodiment, the mount 8, on which the LED as UV radiation source 1 is mounted, is embodied as a rod-like element, the longitudinal axis of which defines a rotation axis. In the present case, the beam collecting optical units 2.1 and 2.2 are also provided once again as TIR lens and glass rod, respectively, but modifications are likewise possible. Furthermore, the ports or positions of the two beam collecting optical units 2.1 and 2.2 are rotated by 180°; the mount 8 is as it were "flipped over" by the control device (see FIG. 1) in order to move to the two ports. FIG. 4A shows a first state, in which the radiation source(s) face(s) one beam collecting optical unit 2.1, while FIG. 4B shows a second state, in which the UV radiation source faces the other beam collecting optical unit 2.2. For the rest, the same explanations as for the second exemplary embodiment are applicable.

FIGS. 5A and 5B show an optical arrangement in accordance with a fourth exemplary embodiment, wherein the UV radiation source 1 embodied as an LED is mounted on a linearly or translationally movable mount 8. Here, too, the beam collecting optical units 2.1 and 2.2 are once again provided purely by way of example as TIR lens and glass rod, respectively, but modifications are likewise possible. The optical axes of the beam collecting optical units 2.1 and 2.2 and also the main radiation direction of the LED are parallel to one another. FIG. 5A shows a first state, in which the UV radiation source 1 has moved to the port of one beam collecting optical unit 2.1 (TIR lens) as a result of driving by the control device 6 (see FIG. 1), while FIG. 5B shows a second state, in which the UV radiation source 1 has moved to the port of the other beam collecting optical unit 2.2 (glass rod) as a result of driving by the control device 6 (see FIG. 1). As in the previous exemplary embodiments, beam delivering optical units such as e.g. mirror arrangements with a free-space optical unit or optical waveguide, effect zones and optionally also beam dividers can be provided.

A second fundamental embodiment will be explained next with reference to FIG. 6. Only differences with respect to the first fundamental embodiment will be described. In FIG. 6, the apparatus 7 has an optical arrangement comprising a mount 8, which is movable by the control device 6 and which accommodates both the UV radiation source(s) 1 and a beam collecting optical unit 2. Both are thus provided with fixed positioning relative to one another on the mount 8. In this exemplary embodiment, the mount 8 can be moved relative to the multiplicity of beam delivering optical units

4.1-4.$n$, to each of which an effect zone 5.1-5.$n$ is respectively assigned as in the case of the first embodiment. By means of the selection of one of the beam delivering optical units 4.1-4.$n$ by means of the control device and subsequent movement of the mount such that the beam collecting optical unit 2 delivers its received and preferably homogenized radiation to the corresponding beam delivering optical unit or couples it into the latter, a desired effect zone 5.1-5.$n$ can thus be supplied with disinfecting UV radiation. With regard to the constitution of the UV radiation sources and also the beam collecting optical unit, the beam delivering optical units and the effect zones, reference can be made to the first embodiment.

FIG. 7 shows a third fundamental embodiment. In this case, provision is made for the beam collecting optical units 2.1-2.2 to be provided on a common mount 8, which can be moved by the control device 6 (and a motor or drive, not shown). Alternatively, the beam collecting optical units 2.1-2.2 can also be provided on a respective dedicated mount and be moved individually. The Fig. shows a stationary UV radiation source 1 and also in each case one beam delivering optical unit 4 and one effect zone 5 in order to illustrate the application. By means of movement of the mount 8, it is possible for the UV radiation source 1 to be assigned to the port of a selected one of the beam collecting optical units 2.1-2.$n$ (that is to say that they can be moved in each case in front of the UV source). Preferably, the beam collecting optical units 2.1-2.$n$ have mutually different optical properties such as, for instance, focal length, etc. In the one effect zone 5, from the one UV radiation source 1 provided it is thereby possible to bring about a desired radiation distribution, for instance in order to vary the intensity distribution in different spatial regions in the effect zone 5, i.e. to be able to effectively disinfect further spatial regions.

FIG. 8 shows a fourth fundamental embodiment. In contrast to the fundamental embodiment shown in FIG. 7, here multiplicities of beam delivering optical units 4.1-4.$n$ and effect zones 5.1-5.$n$ are provided, and the beam collecting optical units 2.1 to 2.$n$ are now adapted for the respective tasks of the effect zones and can each be moved in front of the UV radiation source 1.

A fifth exemplary embodiment, which corresponds to the fundamental embodiments shown in FIG. 7 or 8, is illustrated in FIG. 9. Two beam collecting optical units 2.1 and 2.2 are provided here, purely by way of example, which are mounted on a common mount 8 or are mechanically fixedly connected to one another by said mount. The mount is configured as translationally (or alternatively rotatably etc.) movable relative to the UV radiation source 1 or the LED corresponding to the radiation source and provided on a substrate 11 (e.g. a printed circuit board, etc.). By means of the control device (see FIG. 7 or 8), the port of any of the beam collecting optical units 2.1 and 2.2 can thus be moved in front of the UV LED. As is indicated schematically, the beam collecting optical units 2.1 and 2.2 are two TIR lenses having different characteristics with regard to homogenization or collimation. The optical axes of the beam collecting optical units 2.1 and 2.2 and also the main radiation direction of the UV radiation source are parallel to one another in this exemplary embodiment.

A fifth fundamental embodiment is illustrated in a schematic illustration in FIG. 10. FIGS. 11 to 13B show exemplary embodiments based thereon. In FIG. 10, an optical arrangement in which e.g. only merely one UV radiation source 1 and one beam collecting optical unit 2 are provided in a stationary fashion is provided in the apparatus 7. The beam delivering optical units 4.1-4.$n$ disposed upstream of the effect zones 5.1-5.$n$ also preferably remain stationary. In this embodiment, a beam divider 3 is provided instead, which is configured to divide the UV radiation collected by the beam collecting optical unit 2 and delivered to it into different radiation portions. Alternatively, instead of the beam divider 3 a beam distributor can be provided, which distributes the received UV radiation temporally successively among the individual selected beam delivering optical units 4.1-4.$n$. The two alternatives, simultaneous division and sequential distribution among the respectively selected beam delivering optical units 4.1-4.$n$, can merge into one another if e.g. a deflection mirror oscillates back and forth with high frequency between two setting angles corresponding to the deflection or delivery of the UV radiation to two of the beam delivering optical units 4.1-4.$n$. The beam divider 3 or its UV radiation-distributing alternative can be operated by the control device 6 via a motor. The remaining features correspond here, too, to what has been described with reference to the embodiments above.

FIG. 11 shows a sixth exemplary embodiment based on the embodiment in FIG. 10. The UV radiation source 1 provided on a substrate 11 is configured in a stationary fashion in a port (fitting shape recess) of a TIR lens as beam collecting optical unit 2. A mirror tilted by 45° relative to the optical axis of the beam collecting optical unit 2 serves as a beam divider 3 and is translationally movable in a direction perpendicular to the optical axis of the beam collecting optical unit 2 into the beam path thereof, which can be adjusted by the control device 6. Depending on the degree of spatial overlap with the region of the collimated UV radiation emitted by the beam collecting optical unit 2, as a result a first portion of the UV radiation is transmitted to a first beam delivering optical unit 4.1 or first effect zone 5.1 and a second portion of the UV radiation is deflected toward a second beam delivering optical unit 4.2 or second effect zone 5.2. According to very specific exemplary embodiments, the mirror can also be semitransparent and optionally have filter properties vis-à-vis specific wavelengths. Furthermore, it is also possible, instead of a translation of the beam divider, to displace the unit comprising UV radiation source 1 with substrate 11 and beam collecting optical unit 2, as is indicated schematically by a corresponding arrow in FIG. 11. In the present exemplary embodiment, the radiation portions are very accurately adjustable, and different effect zones can be supplied with UV radiation simultaneously.

FIG. 12 shows a seventh exemplary embodiment. In this case, UV radiation from the UV radiation source 1, for example an LED or a laser, is collected via the beam collecting optical unit 2, illustrated here as a collimation lens, and is reshaped into a parallel beam. The parallelized or collimated beam is subsequently incident on the tiltable or rotatable mirror 32 as one example of a beam distributor. Optionally, beam homogenizing components such as e.g. diffusing elements can also be introduced into the light collecting path. In a first tilt direction, after the reflection at the mirror 32 the radiation is guided to the effect zone 5.1 by a converging lens and an optical fiber, which together form the beam delivering optical unit 4.1. Optionally, further beam shaping optical elements such as e.g. lenses, a microlens array, diffusing plates or the like can be situated at the output of the optical fiber, which moreover is also applicable to all exemplary embodiments described herein. In a second tilt direction, after the reflection at the mirror 32 the radiation is guided via the beam delivering optical unit 4.2, which is of structurally identical construction, for example, to the effect zone 5.2 spatially at a distance from the effect zone

5.1. The control device 6 controlling this via a motor, in particular for example piezoelements, etc., is not illustrated in FIG. 12 for the sake of simplicity.

FIGS. 13A and 13B show an eighth exemplary embodiment based on the embodiment shown in FIG. 10. This involves a specific application of an embodiment to a set-up of an air-conditioning system with a UV radiation source for disinfection and sterilization such as is already known from the document DE 10 2017 220 338, see therein in particular FIG. 4a. In FIGS. 13A and 13B—and also similarly in FIGS. 4a and 4b of DE 10 2017 220 338—an internal module 12 with housing 12a of the air-conditioning system is illustrated, which receives a hot air flow 26 and feeds it to heat exchangers 17 in its interior, said air flow being cooled by said heat exchangers and being blown out of the internal module again as a cooled air flow 28 via a fan 18. A UV radiation source 1 on a mounting plate 10 is fitted between the heat exchangers 17. The UV radiation source 1 is a rod-shaped low-pressure mercury discharge lamp in the present case. Alternatively or additionally, it is also possible to configure LED-based UV radiation sources in a rod-shaped or other arrangement.

In the case of a rod-shaped UV radiation source 1 emitting in all directions, it is then possible to form a simple embodiment of a beam distributor, as illustrated schematically in FIGS. 13A and 13B, for example, from a hollow-cylindrical reflector 33, which however in its cross section does not form a full cylinder but rather only a segment of a cylinder and thus only partially surrounds the UV radiation source 1. The longitudinal axes of the UV radiation source 1 and of the hollow-cylindrical reflector 33 coincide. The reflector 33 is configured as rotatable about its longitudinal axis. By means of a rotation of the reflector 33 controlled by the control device 6 (see FIG. 10) for example (drive not illustrated in FIGS. 13A and 13B), the UV radiation can be guided into different regions of the internal module in a targeted manner, such that a higher radiation intensity is available there if required. The reflector 33 is a specific configuration of a UV radiation-deflecting mirror 32. Types of mirror other than the hollow-cylinder-segment-shaped reflector 33 can also be used.

The reflector 33 for the UV radiation can be configured as completely reflective, such that, depending on the rotational position of the reflector 33, the radiation can optionally be directed completely toward the target region selected. Alternatively, the reflector 32 can also be configured as partly UV-transmitting in order furthermore to be able to emit part of the UV radiation into rear regions as well.

In a first time window, as shown in FIG. 13A, the hollow-cylindrical reflector is situated in a position which directs the majority of the radiation emitted by the UV radiation source 1 (discharge lamp) in the direction of the two upper heat exchangers 17 arranged in a roof-shaped fashion. In a second time window, as shown in FIG. 13B, in a second position of the reflector 33, the UV radiation is directed principally in the direction of the fan 18 and the third, lower heat exchanger 17. The surfaces of the heat exchangers 17 and of the fan 18 typically form sensitive points for germ formation in an air-conditioning system and thus constitute effect zones 5 spatially separated or at a distance in accordance with the embodiments described.

It should be noted that, in the eighth exemplary embodiment, the hollow-cylinder-segment-shaped reflector 32 not only performs the function of the beam distributor, but also simultaneously forms beam collecting optical unit 2 and beam delivering optical unit 4. In the embodiments described above, however, the elements are preferably provided as separate components in each case.

Further modifications or alterations are possible in so far as there is no departure from the scope defined in the appended claims. In the exemplary embodiments above, for example, UV LEDs or UV radiation-emitting low-pressure gas discharge lamps were mentioned as UV radiation sources. However, modifications of the exemplary embodiments and of the embodiments can also use other UV radiation-emitting lamp types, including e.g. UV laser diodes. Moreover, the wavelength of the emitted radiation in the exemplary embodiments is not restricted and can lie in the wavelength intervals of the UV radiation as described in the introduction above.

Furthermore, in so far as the beam collecting optical units, radiation dividers and beam delivering optical units are interpreted as separate components, individual elements from among these can be omitted if the function is concomitantly performed by a respective other element, as is shown by way of example in FIGS. 13A and 13B.

Furthermore, the apparatuses in which the optical arrangement can find application are not restricted to enumerations above. Consideration is furthermore given for instance to systems for water or liquid treatment, or circulation systems in sanitary facilities, swimming pools, saunas, etc., or for instance life support systems in space-based orbiters, etc.

LIST OF REFERENCE SIGNS

1, 1.1-1.n UV radiation source, LED
2, 2-1-2.n Beam collecting optical unit, TIR lens, glass rod
3 Beam divider, mirror
4, 4.1-4.n Beam delivering optical unit, optical waveguide, mirror and/or lens arrangement
5, 5.1-5.n Effect zones
6 Control device
7 Apparatus
8 Mount
10 Mounting plate
11 Substrate
12 Internal module
12a Housing
17 Heat exchanger
18 Fan
24 Sensor
26 Hot air flow
28 Cooled air flow
32 Mirror
33 Hollow-cylinder-segment-shaped reflector
80 Rotation axis
81 Rotary arm, optionally with printed circuit board

The invention claimed is:

1. An optical arrangement for disinfection in apparatuses operating with air or a liquid, comprising:
- at least one radiation source or at least one group of radiation sources, which emits or jointly emit radiation in the ultraviolet wavelength range;
- at least one beam collecting optical unit, which collects the radiation emitted by the radiation source or the group of radiation sources;
- a number of beam delivering optical units, each configured to receive the radiation collected by the at least one beam collecting optical unit; and a number of effect zones spatially separated from one another, into which the radiation delivered via the beam delivering optical units is emitted in order to bring about a disinfecting effect;
wherein
the at least one radiation source or the at least one group of radiation sources, the at least one beam collecting optical unit and/or the number of beam delivering optical units are/is configured such that the radiation emitted by in each case a single radiation source can be delivered to at least two of the effect zones spatially separated from one another simultaneously or with a temporal spacing in each case;
the at least one radiation source or the at least one group of radiation sources is assigned in each case to a beam collecting optical unit and together with the latter forms a unit, and
the unit comprising the at least one radiation source or the at least one group of radiation sources and the respective beam collecting optical unit, on a common mount, is configured as movable between the beam delivering optical units, such that depending on a selection of an effect zone to be disinfected the unit can interact with one of the beam delivering optical units.

2. The optical arrangement as claimed in claim 1, further comprising:
an in particular rotatably configured mirror, which, depending on a tilting, delivers the radiation collected by the beam collecting optical unit optionally to one of the beam delivering units.

3. The optical arrangement as claimed in claim 2, wherein:
the rotatably configured mirror is a hollow-cylinder-segment-shaped reflector configured as rotatable in particular about its center axis, which reflector simultaneously forms the beam collecting optical unit in relation to the radiation source and also the beam delivering optical unit assigned to the beam collecting optical unit, wherein the radiation source itself emits radiation in a full circle of 360° in a plane perpendicular to the center axis.

4. An optical arrangement for disinfection in apparatuses operating with air or a liquid, comprising:
at least one radiation source or at least one group of radiation sources, which emits or jointly emit radiation in the ultraviolet wavelength range;
at least one beam collecting optical unit, which collects the radiation emitted by the radiation source or the group of radiation sources;
a number of beam delivering optical units, each configured to receive the radiation collected by the at least one beam collecting optical unit;
a number of effect zones spatially separated from one another, into which the radiation delivered via the beam delivering optical units is emitted in order to bring about a disinfecting effect; and
a rotatably configured mirror, which, depending on a tilting, delivers the radiation collected by the beam collecting optical unit optionally to one of the beam delivering units;
wherein
the at least one radiation source or the at least one group of radiation sources, the at least one beam collecting optical unit and/or the number of beam delivering optical units are/is configured such that the radiation emitted by in each case a single radiation source can be delivered to at least two of the effect zones spatially separated from one another simultaneously or with a temporal spacing in each case, and
the rotatably configured mirror is a hollow-cylinder-segment-shaped reflector configured as rotatable in particular about its center axis, which reflector simultaneously forms the beam collecting optical unit in relation to the radiation source and also the beam delivering optical unit assigned to the beam collecting optical unit, wherein the radiation source itself emits radiation in a full circle of 360° in a plane perpendicular to the center axis.

5. The optical arrangement as claimed in claim 4, wherein the apparatus:
is a washing machine or a dishwasher; or
is a ventilation and air-conditioning system, in particular an air-conditioning system, a ventilation system, an air circulation system, an air dehumidifier or an air humidifier.

6. The optical arrangement as claimed in claim 4, wherein:
the at least one radiation source or the at least one group of radiation sources is/are embodied as an LED or as LEDs, wherein the LED(s) emits radiation in particular in the wavelength range of UV-C radiation.

7. The optical arrangement as claimed in claim 4, furthermore comprising:
a radiation divider, which divides the radiation collected by the at least one beam collecting optical unit into radiation portions and is configured to selectively deliver the radiation portions to in each case one of the beam delivering optical units.

8. The optical arrangement as claimed in claim 7, wherein:
the radiation divider is configured as adjustable in order to be able to adapt the radiation portions in each case.

9. The optical arrangement as claimed in claim 8, wherein:
the radiation divider is an in particular translationally movably configured mirror, which, depending on a degree of overlap with the radiation collected by the beam collecting optical unit and delivered, couples out a first radiation portion and delivers it to a first beam delivering unit and does not couple out a second radiation portion and thereby delivers it to a second beam delivering unit.

10. The optical arrangement as claimed in claim 4, wherein:
the at least one beam collecting optical unit is a TIR lens.

11. The optical arrangement as claimed in claim 4, wherein:
the beam delivering optical units are represented by optical waveguides or beam paths defined by lens and/or mirror arrangements including combinations thereof.

12. The optical arrangement as claimed in claim 4, wherein:
the effect zones, in the apparatuses, are containers forming UV reactors, surfaces of mounts, pump sumps, interior walls of washing appliances, outlets, heat exchangers and/or water or air filters.

13. An optical arrangement for disinfection in apparatuses operating with air or a liquid, comprising:
at least one radiation source or at least one group of radiation sources, which emits or jointly emit radiation in the ultraviolet wavelength range;

at least one beam collecting optical unit, which collects the radiation emitted by the radiation source or the group of radiation sources;

a number of beam delivering optical units, each configured to receive the radiation collected by the at least one beam collecting optical unit;

a number of effect zones spatially separated from one another, into which the radiation delivered via the beam delivering optical units is emitted in order to bring about a disinfecting effect; and a rotatably configured mirror, which, depending on a tilting, delivers the radiation collected by the beam collecting optical unit optionally to one of the beam delivering units;

wherein the at least one radiation source or the at least one group of radiation sources, the at least one beam collecting optical unit and/or the number of beam delivering optical units are/is configured such that the radiation emitted by in each case a single radiation source can be delivered to at least two of the effect zones spatially separated from one another simultaneously or with a temporal spacing in each case, and wherein the rotatably configured mirror is a hollow-cylinder-segment-shaped reflector configured as rotatable in particular about its center axis, which reflector simultaneously forms the beam collecting optical unit in relation to the radiation source and also the beam delivering optical unit assigned to the beam collecting optical unit, wherein the radiation source itself emits radiation in a full circle of 360° in a plane perpendicular to the center axis.

14. The optical arrangement as claimed in claim 13, wherein:

the at least one radiation source or the at least one group of radiation sources is assigned in each case to a beam collecting optical unit and together with the latter forms a unit, and the unit comprising the at least one radiation source or the at least one group of radiation sources and the respective beam collecting optical unit, on a common mount, is configured as movable between the beam delivering optical units, such that depending on a selection of an effect zone to be disinfected the unit can interact with one of the beam delivering optical units.

* * * * *